US012334302B2

(12) United States Patent
Alonso Gil (10) Patent No.: US 12,334,302 B2
(45) Date of Patent: Jun. 17, 2025

(54) GLOW DISCHARGE CELL AND RELATED GLOW DISCHARGE ASSEMBLY (71) Applicant: Eduardo Alonso Gil, Valladolid (ES)

(72) Inventor: Eduardo Alonso Gil, Valladolid (ES)

( * ) Notice: Subject to any disclaimer, the term of this patent is extended or adjusted under 35 U.S.C. 154(b) by 582 days.

(21) Appl. No.: 17/880,048

(22) Filed: Aug. 3, 2022

(65) Prior Publication Data
US 2024/0047177 A1 Feb. 8, 2024

(51) Int. Cl.
H01J 37/32 (2006.01)
A61L 2/14 (2006.01)
A61L 2/20 (2006.01)
A61L 2/26 (2006.01)

(52) U.S. Cl.
CPC .......... H01J 37/32018 (2013.01); A61L 2/14 (2013.01); A61L 2/202 (2013.01); A61L 2/26 (2013.01); H01J 37/32449 (2013.01); H01J 37/32577 (2013.01); A61L 2202/11 (2013.01)

(58) Field of Classification Search
CPC .......... H01J 37/32018; H01J 37/32449; H01J 37/32577; A61L 2/14; A61L 2/26; A61L 2/202; A61L 2202/11
See application file for complete search history.

(56) References Cited

U.S. PATENT DOCUMENTS

| | | | | |
|---|---|---|---|---|
| RE44,887 E | * | 5/2014 | Whitehouse | ........ H01J 49/0018 436/140 |
| 10,395,892 B2 | * | 8/2019 | Foret | ................. H01J 37/32018 |
| 2008/0315083 A1 | * | 12/2008 | Lubda | ................. G01N 30/7266 422/69 |
| 2011/0042560 A1 | * | 2/2011 | Ouyang | ................... H05H 1/30 250/288 |
| 2015/0311056 A1 | * | 10/2015 | Dovichi | ................ H01J 49/167 250/288 |
| 2017/0025262 A1 | * | 1/2017 | Xu | ........................ G01N 27/447 |
| 2018/0040464 A1 | * | 2/2018 | Cooks | ................. H01J 49/0409 |
| 2019/0019662 A1 | * | 1/2019 | Cooks | ................... H01J 49/165 |

OTHER PUBLICATIONS

Claret, Andree et al., "Reactions of Thermal-Energy Electrons with Organic Compounds", Journal of Chromatography, 1982, pp. 205-210, vol. 247.
Liu, Xing et al., "Plasma induced chemical vapor generation for atomic spectrometry: A review", Spectrochimica Act Part B, 2020, vol. 167.
Sellmeier, Stefan et al., "Dynamic Oil Consumption Measurement of Internal Combustion Engines using Laser Spectroscopy", Technical University of Munich, 2011.
Sellmeier, Stefan et al., "Dynamic Oil Consumption Measurement of Internal Combustion Engines using Laser Spectroscopy", Anal. Chem., 2014, pp. 380-389, vol. 86.
Zheng, Hongtao et al., "Determination of nitrite in water samples using atmospheric pressure glow discharge microplasma emission and chemical vapor generation of NO species", Analytica Chimica Acta, 2018, pp. 100-105, vol. 1001.

* cited by examiner

Primary Examiner — Sean M Luck
(74) Attorney, Agent, or Firm — The Webb Law Firm (57) ABSTRACT The invention relates to a glow discharge cell including a gas evacuation chamber and a gas outlet port integrated in a first bent tube, the branches of which are perpendicular and with different diameters; a gas inlet port formed by a second straight tube along which a plasma is formed and which is partially inserted into the first branch of the first tube; and a primary electrode encapsulated in the first branch of the first tube and facing the second glass tube and being partially inserted therein.

15 Claims, 5 Drawing Sheets

GLOW DISCHARGE CELL AND RELATED GLOW DISCHARGE ASSEMBLY

BACKGROUND OF THE INVENTION

Field of the Invention

The present invention relates to various devices for use in the field of glow discharges, which—as will be explained in detail later—are useful, among others, in the following technical sectors: plasma physics, analytical chemistry, ozone generation, food and pharmaceutical industry, as well as in applications for sterilizing and removing polluting substances.

More particularly, the invention relates to a glow discharge cell and a glow discharge assembly which uses one of said glow discharge cells.

Description of Related Art

Glow discharges are well-known phenomena in the state of the art and usually appear when a gas is subjected to a difference in potential that is sufficiently intense as to cause said gas to be ionized, at least partially, becoming a non-thermal plasma.

Usually, the method used to obtain glow discharges is as follows: an electrical voltage (also known as difference in potential) is applied between two electrodes in a glass tube, which contains a gas at low pressure (from 0.1 mbar to almost 100 mbar). When said voltage exceeds a predetermined threshold value, called "breakdown voltage" and which, according to Paschen's law, depends on the nature of the gas, the distance between electrodes and the pressure of the gas, then the ionization of the gas becomes self-sufficient and the plasma glows with a coloured light.

Glow discharge cells (GDC) are devices similar to those described in the previous paragraph and usually comprise the following elements:

- a chamber in which the plasma is formed and the glow discharge occurs;
- a primary electrode of a conductive metal, frequently made of wolfram, platinum or alloys thereof, provided at a first end of the plasma formation chamber and in contact with the inside of the same;
- a gas inlet port, provided at a second end of the plasma formation chamber and configured as to allow a gas flow (usually comprising air) to access to the inside of the plasma formation chamber; and
- a gas outlet port, in communication with the inside of the plasma formation chamber and intended to lead the gas flow out of the plasma formation chamber. In order for the glow discharge cells described in the previous paragraph to work correctly, a second electrode (or secondary electrode) is usually inserted through the gas inlet port, arranging it so that it remains in contact with the inside of the plasma formation chamber and at a predetermined distance from the primary electrode. Next, the primary electrode and the secondary electrode are connected to a voltage source, capable of causing the formation of plasma. Alternatively, a metal pipe can serve as the secondary electrode.

Glow discharge cells (GDC) can be used in many different applications such as:

- study of various physical laws, such as Paschen's law and Goldstein-Wehrner's law;
- synthesis of chemical compounds. By suitably adjusting various parameters of the glow discharge system (such as applied voltage, intensity, pressure and composition of the gas flow) it is possible to cause said gas flow to react chemically with the primary electrode, with the secondary electrode or even that two different substances present in the gas flow react with each other, giving rise to catalytic synthesis reactions in a homogeneous phase. In addition, the ablated metal of one of the electrodes could also be at least partially involved;
- detection of substances. If a detection device (such as, for example, a spectrometer or spectrophotometer) is added to the glow discharge system, it will be possible to determine whether certain substances or chemical compounds of interest are present, or not, in the gas flow accessing the plasma formation chamber;
- ozone ($O_3$) generation for use as an oxidant or disinfectant (anti-pathogen agent);
- disintegration of substances. As disclosed, for example, in the doctoral thesis "Laserspektroskopische Spurenanalytik von Ölbestandteilen in Abgasen von Verbrennungsmotoren" by Dr. Stephan Sellmeier published by the Faculty of Chemistry at the Technical University of Munich, the formation of a non-thermal plasma from gas flow, is capable of producing the total breakdown/radicalization of the molecules present therein, as well as the oxidation thereof. In fact, as a result of the high kinetic energy (between 1 and 10 eV) that the electrons acquire, the previously existing chemical bonds are broken, giving rise to radicals that react chemically with the oxidative species that are present in the medium.

Further information regarding the use of non-thermal plasma in the disintegration of substances can also be found in Sellmeier, S., Alonso, E., & Boesl, U. (2013). "Dynamic Oil Consumption Measurement of Internal Combustion Engines using Laser Spectroscopy". Analytical Chemistry, 86(1), 380-389. doi:10.1021/ac4015929.

The doctoral thesis written by. Dr. Stephan Sellmeier is considered to be the closest prior art to the present invention and two different examples of glow discharge cells (GDC) are given therein.

In the first of them, a single tube acts as a plasma formation chamber, a gas inlet port and a gas outlet port simultaneously. More particularly, in said glow discharge cell, the gas flow accesses through the left end of the glass tube until it reaches the plasma formation chamber in which the primary electrode, located on the left, and the secondary electrode, located on the right, are arranged. Both electrodes were made of wolfram. The gas flow then comes out through the right end of the glass tube.

Although this first design of the GDC made it possible for the entire gas flow to be exposed to the non-thermal plasma generated in the plasma formation chamber, in practice said glow discharge cell did not work correctly because oxidation rapidly occurred in one of the electrodes that acted as an anode, depositing a yellowish solid (formed mainly by $W_2O_3$) on the electrode itself and the walls of the plasma formation chamber next to the same.

There is therefore a need in the art to develop glow discharge cells in which all the gas flows through the plasma formation chamber and not a very noticeable and rapid degradation of the anode occurs.

To overcome this problem, in said doctoral thesis, Dr. Stephan Sellmeier discloses a second, more advanced glow discharge cell of his own invention (illustrated by way of an example in FIG. 1 attached). Therein, the plasma formation chamber, the gas inlet port and the gas outlet port are formed by a single T-shaped glass tube with equal internal and external diameters. One of the ends of said tube (the right end in FIG. 1) would serve as the gas inlet, while the gas outlet port would be formed in another one of them (the lower end in FIG. 1). Finally, on the external wall of the remaining end (left end in FIG. 1) of the T-shaped tube, the primary electrode would be encapsulated.

Figure 1:
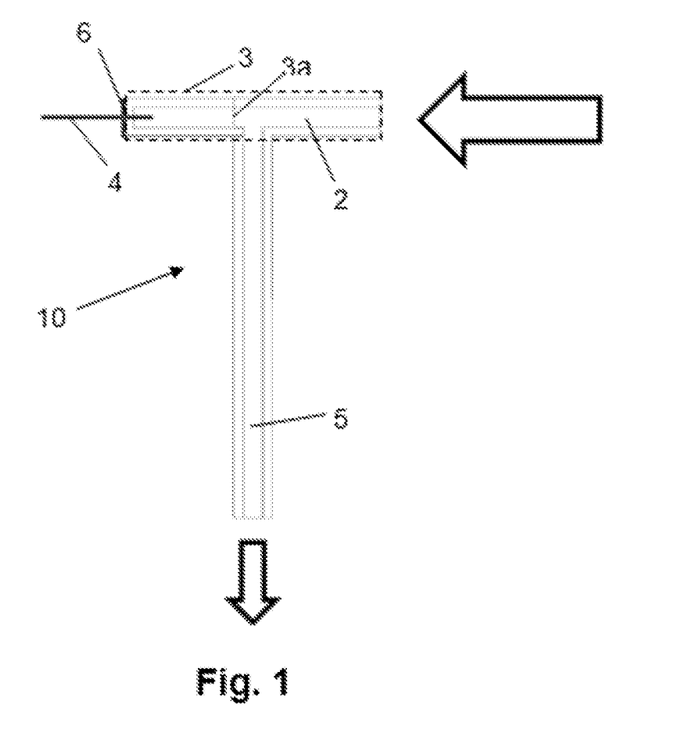
FIG. 1 is a cross-sectional view of a glow discharge cell according to the prior art.

In said glow discharge cell, the plasma formation chamber would be the space between the glass wall in which the primary electrode is encapsulated and the right end of the T-shaped tube through which the gas enters and which, when the device is in use, is attached to a metal conduit in which the secondary electrode is housed. Alternatively, the conduit itself can act as a secondary electrode. In addition, there is a pin-hole, arranged such that it separates the left portion and the right portion of the T-shaped tube, and the purpose of which is that the flow in that chamber is minimal so that they do not accumulate substance giving rise to a memory effect. In this way, the pin-hole prevents a "fluctuating or time-variable" amount of gas (i.e., stochastic) to enter that would produce the random release of gas, creating unexpected peaks (for example, when spectrometric detection was performed).

Although this second glow discharge cell makes it possible to solve the problem of sputtering (ablation or degradation by oxidation) of the secondary electrode, which also acts as an anode, due to the pin-hole, this embodiment of the device has other drawbacks. Thus, for example, in this second GDC, the pin-hole allows the passage of the plasma, but makes it considerably difficult for the gas flow to be exposed, in its entirety, through the plasma formation chamber.

This fact also means that the renewal of the air inside the plasma formation chamber is notably slowed down, which can even cause plasma extinction and stagnation.

In view of this, there is still a need in the sector to develop new glow discharge cells that are capable of simultaneously overcoming all the drawbacks described above.

SUMMARY OF THE INVENTION

In order to address all the drawbacks of the prior art already mentioned above, a first object of the present invention relates to a glow discharge cell, comprising:
  a gas inlet port; intended to allow a gas flow to access;
  a plasma formation chamber integrated in the gas inlet port;
  a primary electrode, in contact with the plasma formation chamber;
  a gas evacuation chamber, intended to allow the relaxation of species formed in the gas and/or the neutralization of free radicals;
  a gas outlet port, which is attached to the gas evacuation chamber and is intended to lead the gas flow out of the glow discharge cell;
characterized in that:
  the gas outlet port and the gas evacuation chamber are formed by a first glass tube, bent in shape, the gas evacuation chamber being provided in a first branch of said tube and the gas outlet port being provided in a second branch of the same, the second branch being smaller in diameter than the first branch and perpendicular thereto;
  the gas inlet port and the plasma formation chamber are formed by a second glass tube, straight and arranged parallel to the first branch of the first tube and being partially inserted into said first branch, so that the second tube is in contact with the inside of the gas evacuation chamber; and
  the primary electrode is encapsulated in a wall of the first branch of the first tube, said primary electrode further being arranged facing the second glass tube and being partially inserted therein.

The specific configuration of the glow discharge cell described above simultaneously has the following advantages over those of the prior art:
  all the gas flow that accesses through the inlet port to the glow discharge cell comes into contact, substantially, with the plasma. In fact, in the devices according to the present invention, the plasma is formed substantially along the entire length of the second straight tube, so that said second tube simultaneously acts as a gas inlet port and a plasma formation chamber;
  the sputtering of the electrode (primary) that acts as an anode is significantly reduced to negligible levels, since work is carried out in positive voltage mode, which causes sputtering to occur in the other electrode, which, being the pipe or an interchangeable part, lengthens the durability of the cell (glass part) and preserves the integrity of the primary electrode, often made of metals such as wolfram (W) or platinum (Pt); and
  the dead space in which a part of the gas flow can accumulate is substantially removed, so the memory effect caused by the existence of a dead space is significantly reduced.

In addition, the fact that the first tube and the second tube are made of glass facilitates the observation of the type of plasma formed and the understanding of the regime in which we are, also enabling the possibility of performing spectrophotometry to examine the properties of the plasma generated based on the substances that are created.

The primary electrode is preferably made of wolfram or an alloy thereof, for example alloys of wolfram with thorium, lanthanum, cerium and/or zirconium. Likewise, the primary electrode can have different diameters, depending on the specific application in question. By way of illustration and not limitation, said diameter can be 0.8 or 1 mm.

Furthermore, even more preferably, the end of the primary electrode farthest from the plasma formation chamber is provided with a safe high-voltage connector that can be connected to a cable with a Bayonet Neill-Concelman ending (SHV-BNC connector), for example, SHV-BNC connectors that support up to 5 KV (marketed under trade names such as Radiall, Ampehnol, and Huhner-shuner), or SHV-BNC connectors that support up to 10 KV (marketed under the Hi-Volt trademark).

The primary electrode can be connected by direct contact to a pin of the safe high-voltage Bayonet Neill-Concelman (SHV-BNC) Jack connector or, alternatively, connected to said pin of the SHV-BNC connector with the interposition of a metal filament of high electrical conductivity, for example, silver, platinum or a metal alloy with an electrical conductivity of the same order of magnitude.

The union of said SHV-BNC connector with the first branch of the first glass tube can be preferably done by means of a dual-component glue of the type marketed, for example, under the Araldite or UHU trademarks.

The incorporation of this type of connector improves the safety of the cell and facilitates the standardization thereof as a high voltage device, avoiding accidents that could cause severe damage.

The first and second glass tubes are preferably made of borosilicate glass and—even more preferably—quartz. The use of quartz would facilitate the use of these glow discharge cells according to the present invention, in applications for detecting substances (present in the gas flow), for example, by spectroscopy in the ranges of visible light (VIS), infrared (IR) and ultraviolet (UV), since in that case the tubes would not absorb radiation within the range of 20 to 2500 nm.

In a particular embodiment of the invention, the wall width of the first branch of the first glass tube and the wall width of the second branch of the same are different from each other. Likewise, the second glass tube can preferably also have the same diameter as the second branch of the first glass tube.

In another preferred embodiment of the present invention, the first branch of the first glass tube is provided with a narrowing at the end closest to the wall encapsulating the primary electrode.

A second object of the invention relates to a glow discharge assembly comprising at least the following elements:
- a glow discharge cell, according to the first aspect of the invention;
- a gas source, in communication with the gas inlet port of the glow discharge cell;
- a secondary electrode arranged coaxially with respect to the gas inlet port of the glow discharge cell and in contact with the plasma formation chamber; and
- a voltage source, connected to the primary electrode and the secondary electrode.

In a preferred embodiment of the invention, the secondary electrode is a hollow metal rod, said hollow metal rod being placed on centring rings, made of insulating material and provided inside the gas inlet port of the glow discharge cell.

The fact that the secondary electrode is hollow has several technical advantages: firstly, it allows the gas coming from the gas source to circulate inside the secondary electrode along the gas inlet port and to the plasma formation chamber. It also allows easy regulation of the gas flow, since in this case it would mainly depend on the internal diameter and the length of the hollow secondary electrode. In addition, this feature has the additional advantage that the hollow electrode can serve as a guide to introduce a wire with a smaller diameter. Alternatively, the wire with a smaller diameter can act as a secondary electrode or material for ablation (especially in applications against pathogens).

Likewise, the fact that the gas circulates inside the secondary electrode makes it easier for the material of which said electrode is made to react with the gas flow or with various substances that have been inserted into said gas flow (such as volatile organic compounds, aerosols and/or pathogens), which may be of special interest in various applications of the glow discharge assembly, for example in those belonging to the field of analytical chemistry, sterilization and the removal of polluting substances (such as will be described in detail later).

Moreover, the fact that the secondary electrode is arranged on centring rings allows the distance to the primary electrode to be easily varied, which confers more versatility to the glow discharge assembly and it is further useful for studying Paschen's law and Goldstein-Wehrner's law. It also allows easy replacement of a secondary electrode that is damaged (for example, by the effect of sputtering) or which, in certain applications of the invention, has been used as a catalyst, for which it has been ablated/sublimated in the gas phase, so that the metal material of said electrode reacts with volatile gaseous substances present in the gas flow.

Said secondary electrode is preferably made of steel and even more preferably, is a hollow steel electrode of those which are marketed under the Swagelake, Parker® or TraleLok® trademarks. Alternatively, the secondary electrode may be made of another metal or metal alloy especially when used as a catalyst (as described in the previous paragraph) or as an antifungal, antibacterial and/or antiviral agent. Preferably, in antifungal, antibacterial and/or antiviral applications, the secondary electrode is made of Copper (Cu), Silver (Ag) or alloys thereof, the effectiveness of which has already been demonstrated. Likewise, the secondary electrode can be made of platinum or a metal alloy with an electrical conductivity of the same order of magnitude.

In a more preferred embodiment of the glow discharge assembly according to the invention, the secondary electrode is a metal rod, such as the one described in the previous paragraphs and wherein, in addition, the end of said secondary electrode farthest from the plasma formation chamber is connected to a T-shaped conduit, at least one of the remaining ends of the T-shaped conduit in turn being connected to a gas source. The metal rod may optionally be hollow so that the gas flow enters through the opening of said hollow metal rod. Alternatively, the metal rod can be solid, in which case the gas flow enters through a parallel branch.

Likewise, the metal rod, in addition to being hollow, can also be configured to act as a catalyst, so that a portion of the metal material of which it is composed is ablated/sublimated and reacts with the volatile reactive compounds present in the gas flow.

Said T-shaped connection increases the versatility of the assembly of the invention. Thus, for example, in a particularly preferred configuration, the secondary electrode is connected to a first end of the T-shaped conduit, while a second end of the T-shaped conduit (that is facing the secondary electrode) is provided, either with a plug, or with a hollow element. Lastly, a third end of the T-shaped conduit (which is perpendicular to the secondary electrode) is in turn connected to a gas source provided with a flow regulator.

In the embodiment of the invention described in the previous paragraph, if the second end of the T-shaped conduit is provided with a plug, said plug would prevent the entry of air, so that in that case all the gas that arrived to the gas inlet port would be the one coming from the third end of the T-shaped conduit. On the contrary, if the second end of the T-shaped conduit were provided with a hollow element, two different gas streams could access the gas inlet port: the first coming from the third end of the T-shaped conduit and the second coming from the second end of the same.

If, in addition, the metal rod were hollow and configured to act as a catalyst, we could have two different gaseous components that would react in the plasma with the sublimated metal itself, coming from the hollow metal rod that acts as a secondary electrode.

The T-shaped connection can also fulfil a double air inlet function, which is especially useful in purification applications. Thus, for example, the hollow rod can transport a predetermined amount of gas, while the perpendicular rod can increase the total flow from 0 to a certain value that results from having an open needle or solenoid (electric) valve fully open.

The hollow element at the second end could also be used, alternatively, to introduce various substances, not necessarily gaseous, and for them to mix with the gas stream coming from the third end of the T-shaped conduit. Thus, in applications for sterilizing and removing polluting substances, said substances could be, for example, aerosols, polluting particles and/or pathogens that would be mixed with the gas stream from the third end of the T-shaped conduit and would access the glow discharge cell through the gas inlet port. Once in the plasma formation chamber, due to the high difference in potential between the primary electrode and the secondary electrode (which are connected to the voltage source terminals), a portion of the gas would be ionized giving rise to a non-thermal plasma. The generated plasma is capable of breaking down both organic and inorganic matter, degrading large molecules to the fundamental molecular gases thereof, as disclosed, for example, in the aforementioned doctoral thesis by Dr. Eduardo Alonso Gil.

In light of the foregoing, a third object of the present invention relates to a sterilization system comprising a glow discharge assembly provided with at least:
- a glow discharge cell, according to the first aspect of the invention;
- a gas source, in communication with the gas inlet port of the glow discharge cell;
- a secondary electrode arranged coaxially with respect to the gas inlet port of the glow discharge cell and in contact with the plasma formation chamber; and
- a voltage source, connected to the primary electrode and the secondary electrode.

wherein said system is configured such that the gas flow from the gas source is mixed with a stream of polluting particles, before accessing the plasma formation chamber of the glow discharge cell.

Broadly speaking, the operation of the sterilization system of the present invention is as follows: as already described, the stream of polluting particles is mixed (for example, due to a T-shaped conduit like those described above) with the flow of gas from the gas source before said gas accesses the plasma formation chamber of the glow discharge cell. Subsequently, the gas stream mixed with the polluting particles is led to the plasma formation chamber, where, according to the method explained above, a portion of the gas would be ionized, giving rise to a non-thermal plasma that would break down the polluting particles.

In a preferred embodiment of the sterilization system according to the present invention, the secondary electrode is a copper or copper alloy electrode. The use of these metals is preferred because copper (Cu) has antibacterial properties.

A fourth object of the present invention relates to a reactor system comprising a glow discharge assembly provided with at least:
- a glow discharge cell, according to the first aspect of the invention;
- a gas source, in communication with the gas inlet port of the glow discharge cell;
- a secondary electrode arranged coaxially with respect to the gas inlet port of the glow discharge cell and in contact with the plasma formation chamber; and
- a voltage source, connected to the primary electrode and the secondary electrode.

wherein said system is configured such that the gas flow from the gas source is mixed with reactive particles, before accessing the plasma formation chamber of the glow discharge cell.

Essentially, the operation of the reactor system of the present invention is as follows: the reactive compounds are mixed with the gas flow coming from the gas source before said gas accesses the gas inlet port of the glow discharge cell. Subsequently, the gas stream mixed with the reactive compounds would be led to the plasma formation chamber, where a portion of the gas would be ionized, giving rise to a non-thermal plasma. The energy of said plasma would be high enough to cause the reactive compounds to react, for example, giving rise to reactions in the gas phase and in the case where there is a metal element from ablation, a catalytic reaction is also possible. In this particular application of the invention, the secondary electrode is preferably hollow and is configured to act as a catalyst, a portion of the metal material of said electrode being ablated/sublimated so that it reacts with the volatile reactive compounds present in the gas flow.

In a preferred embodiment of the reactor system of the invention, the reactive particles are arranged on the secondary electrode, the secondary electrode further being a hollow metal rod placed on centring rings, made of insulating material and provided inside the gas inlet port of the glow discharge cell. A particular case of this embodiment of the invention consists in the reagent being a metal or metal alloy and the secondary electrode being made of said metal or metal alloy. In this case, the metal or metal alloy particles would detach from said electrode as a result of the ablation and would be mixed with the gas flow at the gas inlet port.

Alternatively, the reactive compounds can be mixed in another manner with the gas flow coming from the gas source, for example, due to a T-shaped conduit as described above.

A fifth object of the present invention relates to a detector system comprising a glow discharge assembly provided with at least:
- a glow discharge cell, according to the first aspect of the invention;
- a gas source, in communication with the gas inlet port of the glow discharge cell;
- a secondary electrode arranged coaxially with respect to the gas inlet port of the glow discharge cell and in contact with the plasma formation chamber; and
- a voltage source, connected to the primary electrode and the secondary electrode;
- being further provided with a detection unit, configured to detect at least one region of the spectrum of the radiation emitted by the plasma produced in the plasma formation chamber.

Essentially, the operation of the detector system of the present invention is as follows: the detector unit is configured to detect at least one region of interest of the spectrum of the radiation emitted by the plasma (which is produced in the plasma formation chamber). From the information on the emission spectrum of the plasma, obtained by said unit, it is possible to deduce whether or not certain chemical substances of interest are present in the gas of interest, since said plasma is generated from the gas flow coming from the gas source and which accesses the glow discharge cell from the gas inlet port. This would also allow the products of a reaction to be monitored, through the spectra thereof, while the conditions of the plasma: pressure, tension and intensity, are varied.

The detection unit may comprise, for example, a spectrometer and/or a spectrograph.

BRIEF DESCRIPTION OF THE DRAWINGS

To complete the present description of the invention and in order to better understand the technical features of several preferred embodiments of the same, the following figures are attached, by way of illustration and not limitation.

The following is a list of the numerical references used in said figures:

1. First glass tube (bent in shape);
1a First branch of the first tube;
1b Second branch of the first tube;
2. Gas inlet port (in the present invention it is a second straight glass tube);
3. Plasma formation chamber;
3a. Wall with pin-hole;
4. Primary electrode;
5. Gas outlet port (in the present invention it is the second branch of the first tube);
6. Wall that encapsulates the primary electrode;
7. Narrowing (of the first branch of the first glass tube);
8. Gas evacuation chamber;
9. Sealing gasket;
10. Glow discharge cell;
11. Gas source;
12. Voltage source;
13. Insulating centring rings;
14. Secondary electrode;
15. Flow regulator;
16. Plasma-forming region;
17. T-shaped conduit;
18. Hollow element.

DESCRIPTION OF THE INVENTION

Next, a description of various preferred embodiments of the present invention is made.

Throughout the description that follows, as well as in the attached figures, the elements with equal or similar functions will be designated with the same numerical references.

As already stated, FIG. 1 is a cross-sectional view of an already known glow discharge cell 10 that was disclosed in the doctoral thesis "Laserspektroskopische Spurenanalytik von Ölbestandteilen in Abgasen von Verbrennungsmotoren" by Dr. Stephan Sellmeier.

Said glow discharge cell 10 comprises a single T-shaped glass tube, a first end of said tube being the gas inlet port 2 and a second end of the same being the gas outlet port 5. The third end of the tube is provided with a wall 6 in which the primary electrode 4 is encapsulated. In this prior art cell 10, the internal and external diameters of all the ends of the T-shaped tube are identical to each other.

Furthermore, FIG. 1 illustrates the movement of gas flow through the glow discharge cell 10 by means of arrows.

In this particular case, the plasma formation chamber 3 would be the space comprised between the glass wall 6 in which the primary electrode is encapsulated and the right end of the gas inlet port 2 which, when the device is in use, is attached to a metal conduit in which the secondary electrode is housed. In addition, a wall 3a having a pin-hole is provided, leaving only a small hollow space with a 0.5 mm cross section that links both portions of the T-shaped tube. Said pin-hole allows the passage of the plasma to the end of the tube 2 reaching the steel conduit.

Figure 2:
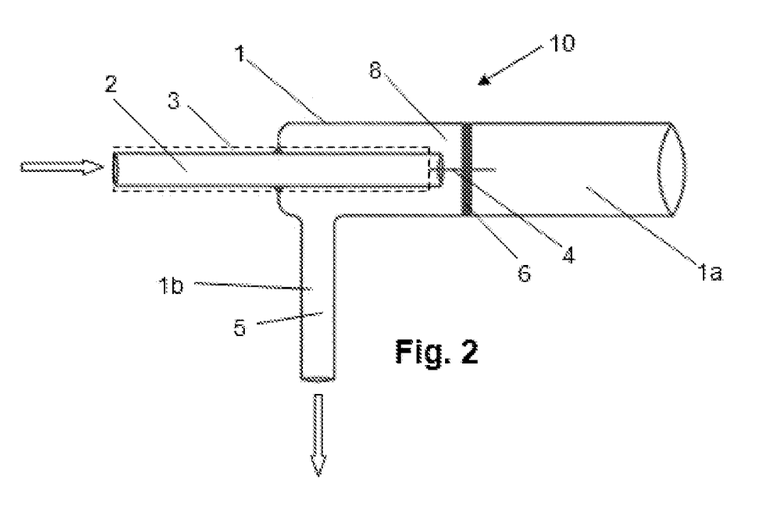
FIG. 2 is a cross-sectional view of a glow discharge cell according to a first embodiment of the present invention.

FIG. 2 shows a first embodiment of a glow discharge cell 10 according to the present invention.

Said glow discharge cell 10 comprises a first glass tube 1, bent in shape, provided with a first branch 1a and a second branch 1b that are mutually perpendicular to each other. In the particular embodiment of the invention shown in FIG. 2, the first branch 1a has an external diameter of 17 mm and a wall thickness of 1.2 mm, while the second branch 1b has an external diameter of 6 mm and a wall thickness of 1.5 mm.

The first branch 1a is provided with a wall 6 that prevents the passage of gas and simultaneously encapsulates the primary electrode 4, made of wolfram.

Figure 3:
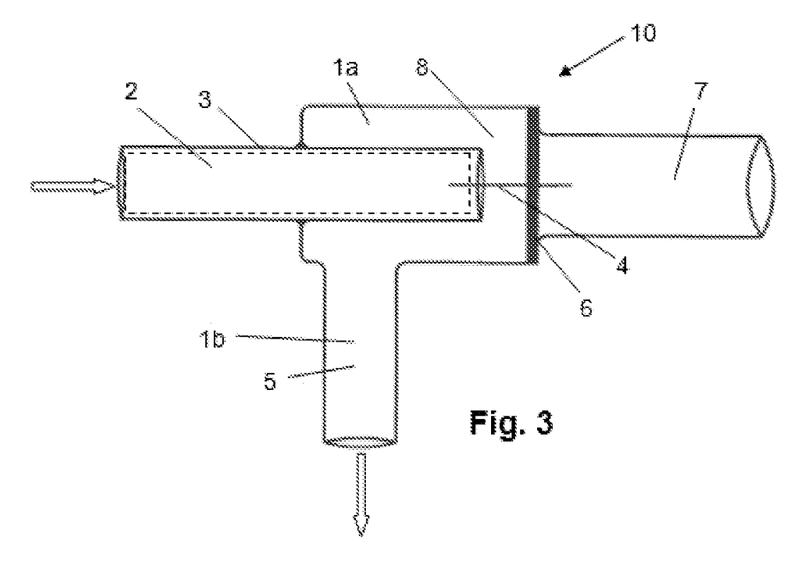
FIG. 3 is a cross-sectional view of a glow discharge cell according to a second embodiment of the present invention.

Both in the embodiment shown in FIG. 2, as in that of FIG. 3, the wall 6 is a straight wall. However, the present invention expressly contemplates the possibility that said wall 6 has a different shape and, in particular, that the wall 6 protrudes transversely towards the gas inlet port in the area adjacent to the point of contact of the wall 6 with the primary electrode 4. In fact, the shape of the wall 6 can be varied depending on the specific application of the invention in question, thus varying the degree of tightness and the gas flow rate.

In addition, the first branch 1a is also provided with the gas evacuation chamber 8, while the second branch 1b serves as the gas outlet port 5.

The gas inlet port 2 is a second straight glass tube that also acts as the plasma formation chamber 3 (indicated with broken lines in FIG. 2). In this particular embodiment of the invention, the gas inlet port 2 has the same dimensions as the second branch 1b of the first tube 1, i.e., the external diameter thereof is 6 mm and the wall thickness thereof is 1.5 mm.

Said second tube 2 is arranged parallel to the first branch 1a of the first tube 1 and is inserted into said first branch 1a, so that the gas inlet port 2 is in contact with the inside of the gas evacuation chamber 8 and facing the primary electrode 4.

As in the previous case, FIG. 2 also illustrates the movement of gas flow through the glow discharge cell 10 by means of arrows.

FIG. 3 shows a second embodiment of a glow discharge cell 10 according to the present invention similar to the previous one, reason for which the elements that are common to both embodiments of the invention will not be described again.

However, in the embodiment illustrated in FIG. 3, the first branch 1a of the first tube 1 is provided with a narrowing 7.

Furthermore, in this second embodiment of the invention, the dimensions of the tubes 1 and 2 vary from those of the first embodiment. In fact, they are about 100% larger. Thus, in the embodiment shown in FIG. 3, the first branch 1a has an external diameter of 26 mm and a wall thickness of 2 mm, while the second branch 1b has an external diameter of 12 mm and a wall thickness of 1.5 mm. The narrowing 7 in turn has an external diameter of 17 mm and a wall thickness of 1.2 mm.

Moreover, the second glass tube 2 (i.e., the gas inlet port) also has, in this particular embodiment, the same dimensions as the second branch 1b of the first tube 1, i.e.: the external diameter thereof is 12 mm and the wall thickness thereof is 1.5 mm.

Figure 4:
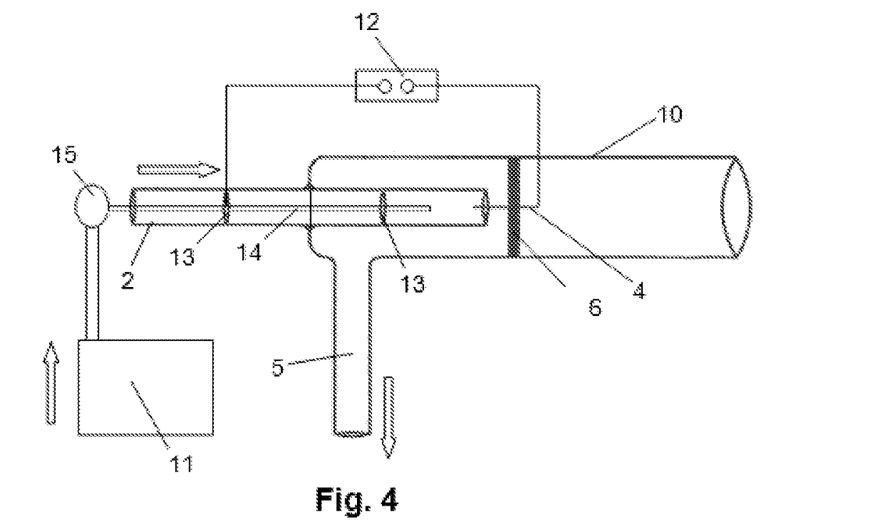
FIG. 4 is a schematic view, not to scale, of a first embodiment of a glow discharge assembly according to the present invention.

FIG. 4 schematically shows an embodiment of a glow discharge assembly according to the present invention which, in this particular case, is provided with a glow discharge cell 10 like the one shown in FIG. 2. The assembly is further provided with a secondary electrode 14 formed by a hollow stainless steel rod. Alternatively, the secondary electrode 14 may be formed by a different conductive material, such as steel or copper.

The secondary electrode 14 is arranged on centring insulating rings 13, preferably made of Teflon or ceramic. Said insulating rings 13 are provided inside the gas inlet port of the glow discharge cell. In an alternative embodiment of the invention, the centring insulating rings 13, preferably made of Teflon or ceramic, are arranged inside a Swagelok conduit in turn attached to a Cajon Ultra Torr which is fastened to the second tube 2 of the cell 10.

A gas flow from a gas source 11 circulates through the hollow secondary electrode 14, which is provided with a flow regulator 15. Alternatively, the hollow secondary electrode 14 may be exposed to air, as is the case, for example, in air purification applications.

In order for plasma formation to be possible, both the primary electrode 4 and the secondary electrode 14 are electrically connected to a voltage source 12.

Figure 5:
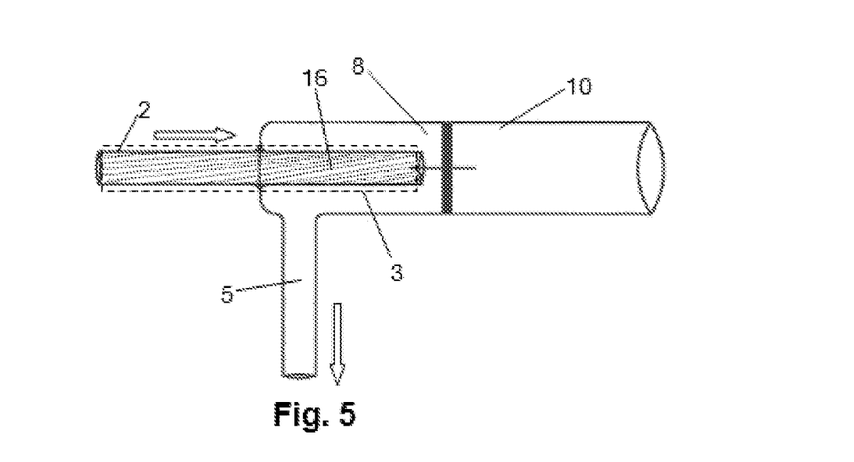
FIG. 5 is a schematic view, not to scale, illustrating how the plasma is formed in the glow discharge cell of the invention.

FIG. 5 is a view that schematically illustrates the manner in which the plasma is formed in the glow discharge cell 10 when the glow discharge assembly is in operation. Thus, as the gas flow circulates in the direction indicated by the arrows, a portion of said gas would be ionized due to the effect of the difference in potential to which it is subjected, giving rise to a non-thermal plasma that would accumulate in the region 16, which in the devices of the invention essentially covers the entire length of the tube 2), and which is schematically represented with dotted lines in FIG. 5.

Figure 6:
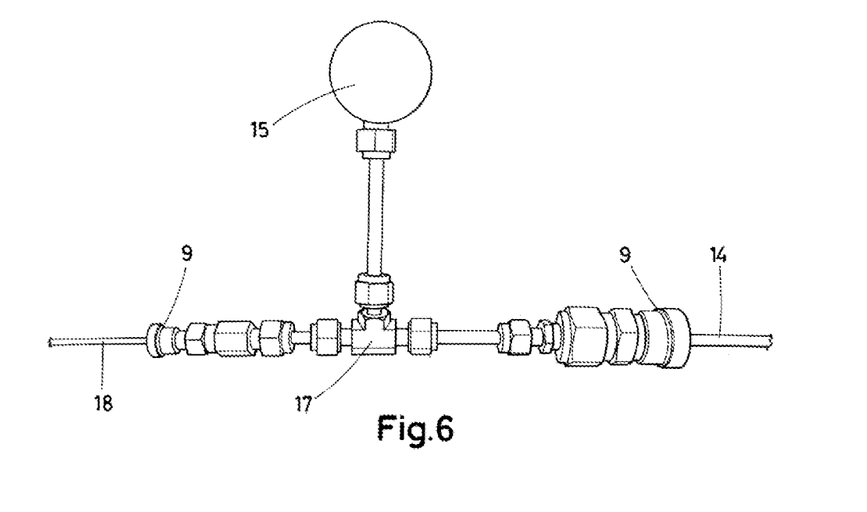
FIG. 6 is a side elevation view of a secondary electrode that forms part of a glow discharge assembly according to the present invention.

Lastly, FIG. 6 shows a hollow secondary electrode 14, for use in a glow discharge assembly according to the present invention. The hollow secondary electrode 14 is similar to the one in FIG. 4, but with the proviso that said electrode is contained in a T-shaped conduit 17, marketed by the Swagelog® trademark. Alternatively, T-shaped conduits marketed by other different trademarks, such as Parker® or Trale Loc®, can also be used. The end first passes through a larger Ultra Torr Cajon which fastens the cell.

The second end of the T-shaped conduit 17 is in turn connected to a hollow element 18, in this particular case an Ultra Torr Cajon, while the third end is connected to a flow rate regulator 15 of a gas source. Alternatively, hollow element 18, can be an integral part of the secondary electrode 14. Gaskets 9 intended to guarantee the tightness of the different connections are also interposed, which in this particular embodiment of the invention are Ultra Torr model gaskets, marketed by the Swagelog® trademark.

The configuration illustrated in FIG. 6 allows the gas flow that accesses through the third end of the T-shaped conduit 17 to be mixed, if desired, with a second gas stream that accesses the second end of the same through the hollow element 18.

This configuration is especially useful to be able to implement the sterilization system, the reactor system and the detector system according to the present invention, since, respectively and depending on the specific application for which it is used, polluting particles, reactive particles or particles of interest the composition of which is to be studied can be added to said second gas stream.

The invention should not be limited to the particular embodiments described herein. Persons skilled in the art can develop other embodiments in view of the description made herein. As a result, the scope of protection of the present invention is exclusively defined by the claims that follow.

The invention claimed is:
1. A glow discharge cell, comprising:
 a gas inlet port, intended to allow a gas flow to access;
 a plasma formation chamber integrated in the gas inlet port;
 a primary electrode, in contact with the plasma formation chamber;
 a gas evacuation chamber, intended to allow the relaxation of species formed in the gas and/or the neutralization of free radicals; and
 a gas outlet port, which is attached to the evacuation chamber and is intended to lead the gas flow out of the glow discharge cell;
 wherein:
 the gas outlet port and the gas evacuation chamber are formed by a first glass tube, bent in shape, the plasma formation chamber being provided in a first branch of the first glass tube and the gas outlet port being provided in a second branch of the first glass tube, the second branch being smaller in diameter than the first branch and perpendicular thereto;
 the gas inlet port and the plasma formation chamber are formed by a second glass tube, straight and arranged parallel to the first branch of the first glass tube and being partially inserted into said first branch, so that the second glass tube is in contact with the inside of the gas evacuation chamber; and
 the primary electrode is encapsulated in a wall of the first branch of the first glass tube, said primary electrode further being arranged facing the second glass tube and being partially inserted therein.

2. The glow discharge cell according to claim 1, wherein an end of the primary electrode that is farthest from the plasma formation chamber is provided with a safe high-voltage connector that can be connected to a cable with a Bayonet Neill-Concelman ending (SHV-BNC).

3. The glow discharge cell according to claim 1, wherein the primary electrode is connected to a pin of a safe high-voltage Bayonet Neill-Concelman Jack connector, with the interposition of a silver, platinum or metal alloy filament with an electrical conductivity of the same order of magnitude.

4. The glow discharge cell according to claim 1, wherein the wall width of the first branch of the first glass tube and the wall width of the second branch of the first glass tube are different from each other.

5. The glow discharge cell according to claim 1, wherein the second glass tube has the same diameter as the second branch of the first glass tube.

6. The glow discharge cell according to claim 1, wherein the first branch of the first glass tube is provided with a narrowing at an end closest to the wall encapsulating the primary electrode.

7. A glow discharge assembly comprising at least the following elements:
 a glow discharge cell, according to claim 1;
 a gas source, in communication with the gas inlet port of the glow discharge cell;
 a secondary electrode arranged coaxially with respect to the gas inlet port of the glow discharge cell and in contact with the plasma formation chamber; and
 a voltage source, connected to the primary electrode and the secondary electrode.

8. The glow discharge assembly according to claim 7, wherein the secondary electrode is a hollow metal rod, said hollow metal rod being arranged on insulating centring rings, provided inside the gas inlet port of the glow discharge cell.

9. The glow discharge assembly according to claim 7, wherein an end of the secondary electrode farthest from the plasma formation chamber is connected to one end of a T-shaped conduit having three ends, and at least one remaining end of the T-shaped conduit in turn is connected to a gas source.

10. The glow discharge assembly according to claim 9, wherein:
the secondary electrode is connected to a first end of the T-shaped conduit;
the second end of the T-shaped conduit is facing the secondary electrode and is provided either with a plug or with a hollow element; and
the third end of the T-shaped conduit is perpendicular to the secondary electrode and is connected to a gas source provided with a flow regulator.

11. A sterilization system comprising a glow discharge assembly provided with at least:
a glow discharge cell, according to claim 1;
a gas source, in communication with the gas inlet port of the glow discharge cell;
a secondary electrode arranged coaxially with respect to the gas inlet port of the glow discharge cell and in contact with the plasma formation chamber; and
a voltage source, connected to the primary electrode and the secondary electrode;
wherein said system is configured such that the gas flow from the gas source is mixed with a stream of polluting particles, before accessing the plasma formation chamber of the glow discharge cell.

12. The sterilization system according to claim 11, wherein the secondary electrode is a copper, copper alloy, silver, silver alloy or metal alloy electrode with an electrical conductivity of the same order of magnitude.

13. A reactor system comprising a glow discharge assembly provided with at least:
a glow discharge cell, according to claim 1;
a gas source, in communication with the gas inlet port of the glow discharge cell;
a secondary electrode arranged coaxially with respect to the gas inlet port of the glow discharge cell and in contact with the plasma formation chamber; and
a voltage source, connected to the primary electrode and the secondary electrode;
wherein said system is configured such that the gas flow from the gas source is mixed with reactive particles, before accessing the plasma formation chamber of the glow discharge cell.

14. The reactor system according to claim 13, wherein the reactive particles are arranged on the secondary electrode, said secondary electrode being a hollow metal rod placed on centring rings made of insulating material and provided inside the gas inlet port of the glow discharge cell.

15. A detector system comprising a glow discharge assembly provided with at least:
a glow discharge cell, according to claim 1;
a gas source, in communication with the gas inlet port of the glow discharge cell;
a secondary electrode arranged coaxially with respect to the gas inlet port of the glow discharge cell and in contact with the plasma formation chamber; and
a voltage source, connected to the primary electrode and the secondary electrode;
being further provided with a detection unit, configured to detect at least one region of the spectrum of the radiation emitted by the plasma produced in the plasma foundation chamber.

* * * * *